United States Patent [19]

Yamamoto et al.

[11] Patent Number: 5,268,492

[45] Date of Patent: Dec. 7, 1993

[54] OPTICALLY ACTIVE DIPHOSPHINES, INTERMEDIATES THEREOF, AND PROCESSES FOR PRODUCTION THEREOF

[75] Inventors: Keiji Yamamoto, Yokohama; Masahiro Miyazawa, Yokosuka; Satoru Momose, Kawasaki, all of Japan

[73] Assignee: Mitsui Toatsu Chemicals, Inc., Tokyo, Japan

[21] Appl. No.: 935,714

[22] Filed: Aug. 27, 1992

[30] Foreign Application Priority Data

Aug. 30, 1991 [JP] Japan .................. 3-219088
Aug. 30, 1991 [JP] Japan .................. 3-219089

[51] Int. Cl.⁵ .............. C07D 307/91; C07F 15/00; C07F 9/02
[52] U.S. Cl. ......................... 549/460; 556/21; 556/136; 568/8; 568/17; 568/338; 568/365; 568/367
[58] Field of Search .............. 556/21, 136; 568/8, 568/17, 338, 365, 367; 549/460

[56] References Cited

FOREIGN PATENT DOCUMENTS 1170025 11/1969 United Kingdom .

OTHER PUBLICATIONS

Chem. Abstracts CA 114(19):184 937n (Miyazawa et al.) May 13, 1991.
Chem. Abstracts CA 114(21):207 458y (Casey et al.) May 27, 1991.
Casey et al., The Journal of Organic Chemistry, vol. 55, 1990, p. 1394t.
Casey et al., J. Org. Chem., 55, 1394–96 (1990).
Miyazawa et al., SYNLETT, 711–712 (1990).

*Primary Examiner*—José G. Dees
*Assistant Examiner*—Porfirio Nazario
*Attorney, Agent, or Firm*—Millen, White, Zelano, & Branigan

[57] ABSTRACT

An optically active diphosphine having a bicyclo[2.2.1-]heptane of the formula

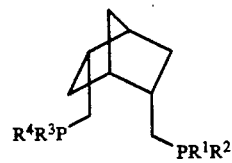

or

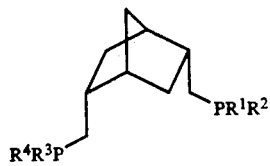

where $R^1$, $R^2$, $R^3$ and $R^4$ are difined in the specification and a metal complex comprising said optically active diphosphine are disclosed. A process for producing or purifying said optically active diphosphine is disclosed.

4 Claims, No Drawings

OPTICALLY ACTIVE DIPHOSPHINES, INTERMEDIATES THEREOF, AND PROCESSES FOR PRODUCTION THEREOF

BACKGROUND OF THE INVENTION

1. Field of the Invention

The present invention relates to an optically active diphosphine having a bicyclo[2.2.1]heptane skeleton, an optically active intermediate for the production thereof and processes for producing these compounds.

2. Description of the Related Art

In syntheses of many organic compounds having an asymmetric carbon such as used for medicines, agricultural chemicals and the like, asymmetric syntheses which produce useful enantiomers only and the production or unnecessary use of less pharmacologically active medicines, thus, saving resources and protecting environment and ecosystem, have been in high demand.

Heretofore, asymmetric hydrolysis using microorganisms or enzymes and asymmetric esterification has been used as a technique of asymmetric synthesis.

However, catalytic asymmetric syntheses capable of producing a large amount of optically active compounds from a small amount of chiral source are recently most attractive.

As the important chiral source, there are used optically active metal complexes.

There are known various means for bringing metal complexes to an optically active environment.

An example of such means is to use optically active diphosphine ligands represented by (S)- or (R)-2,2'-bis (diphenylphosphino)-1,1'-binaphthyl (abbreviated as "(S)- or (R)-BINAP").

In particular, phosphines can stably coordinate to various metals, and can be widely used as effective ligands in many homogeneous metal catalytic reactions.

There are many known homogeneous catalytic asymmetric reactions using an optically active phosphine as an effective ligand, for example, synthesis of optically active amino acids by an asymmetric hydrogenation reaction of dehydroamino acid; synthesis of l-menthol through an asymmetric isomerization reaction; and preparation of monomers for biodecomposition high polymers by an asymmetric hydrogenation of acetoacetic acid esters.

In catalytic asymmetric reactions, there is required a special catalytic property, that is, enantio-selectivity as well as ordinary catalytic properties such as reaction activity, selectivity and the like.

In order to improve these properties, there has been recent active investigation, in particular, in the development of optically active diphosphines having the capability of bidentate coordination.

There has never been synthesis of stereochemically controlled optically active diphosphines (such as those in the present invention) having the capability of bidentate coordination.

Syntheses of racemic modifications of such diphosphines are described only in C. P. Casey et al: J. Org. Chem., 55, 1394-96 (1990) and the present inventors: SYNLETT, 711-712 (1990).

In each of these processes for the preparation of the racemic modification, there is not an appropriate compound or method suitable for optical resolution in mid course of the preparation, and in addition, the resulting racemic modification itself can not be easily optically resolved.

Indeed, the above-mentioned methods are useful for producing the racemic modification, but the methods are not suitable for the production of optically active compounds which are the subject matter of the present invention.

SUMMARY OF THE INVENTION

An object of the present invention is to provide a novel optically active diphosphine having a capability of bidentate coordination.

Another object of the present invention is to provide a process for producing an optically active diphosphine having a capability of bidentate coordination.

A further object of the present invention is to provide an intermediate for producing an optically active diphosphine.

According to a first aspect of the present invention, there is provided an optically active diphosphine having a bicyclo[2.2.1]heptane skeleton of the formula (1) or (2)

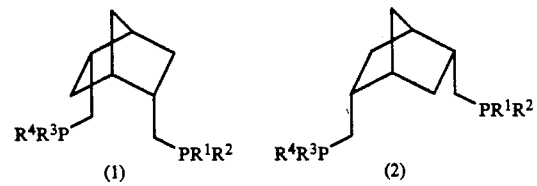

where $R^1$, $R^2$, $R^3$ and $R^4$ are similar or dissimilar and selected from the group consisting of alkyl having 1–8 carbon atoms, aryl having 6–18 carbon atoms, and aralkyl having 7–18 carbon atoms, and $R^1$ and $R^2$ and/or $R^3$ and $R^4$ may be bonded directly or through at least one atom other than phosphorus to form a ring together with the phosphorus to which $R^1$ and $R^2$, or $R^3$ and $R^4$ attach.

According to a second aspect of the present invention, there is provided a metal complex which comprises an optically active diphosphine having the bicyclo[2.2.1]heptane skeleton represented by the formula (1) or (2) above as a ligand.

According to a third aspect of the present invention, there is provided an intermediate for producing the optically active diphosphine of the formula (1) or (2) above, that is, an optically active diphosphine oxide having a bicyclo[2.2.1]heptane skeleton of the formula (3) or (4)

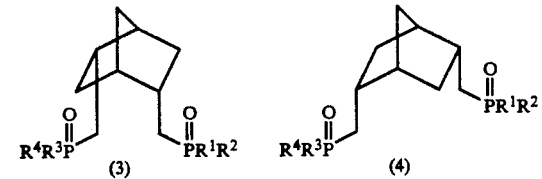

where $R^1$, $R^2$, $R^3$ and $R^4$ are similar or dissimilar and selected from the group consisting of alkyl having 1–8 carbon atoms, aryl having 6–18 carbon atoms, and aralkyl having 7–18 carbon atoms, and $R^1$ and $R^2$ and/or $R^3$ and $R^4$ may be bonded directly or through at least one atom other than phosphorus to form a ring together with the phosphorus to which $R^1$ and $R^2$, or $R^3$ and $R^4$ attach, an optically active keto-ether of the formula (5) or (6)

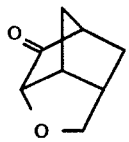
(5)

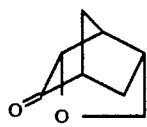
(6)

an optically active keto-ol of the formula (7) or (8)

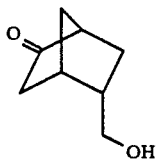
(7)

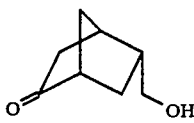
(8)

or an optically active diol having a bicyclo[2.2.1]heptane skeleton of the formula (9) or (10)

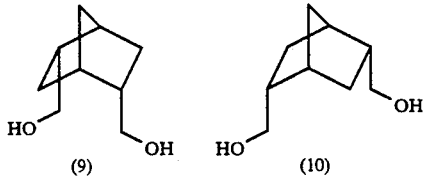
(9)  (10)

According to the fourth aspect of the present invention, there is provided a process for producing an optically active diphosphine having a bicyclo[2.2.1]heptane skeleton of the formula (1) or (2) as above which comprises converting the hydroxyl groups of an optically active diol having a bicyclo[2.2.1]heptane skeleton of the formula (9) or (10) as above to leaving groups and substituting the leaving groups with a phosphine compound.

According to a fifth aspect of the present invention, there is provided a process for producing an optically active keto-ether of the formula (5) or (6) as above which comprises epoxidizing an optically active endo-5-hydroxymethylbicyclo[2.2.1]hept-2-ene of the formula (11) or (12)

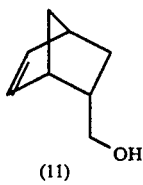
(11)
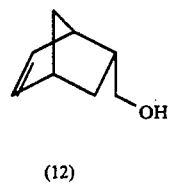
(12)

subjecting the resulting epoxide to intramolecular cyclizing etherification and oxidizing the hydroxyl group.

According to a sixth aspect of the present invention, there is provided a process for producing an optically active keto-ol of the formula (7) or (8) as above which comprises ring opening of an optically active keto-ether of the formula (5) or (6) as above.

According to a seventh aspect of the present invention, there is provided a process for producing an optically active diol having a bicyclo[2.2.1]heptane skeleton of the formula (9) or (10) as above which comprises converting the ketone groups of an optically active keto-ol of the formula (7) or (8) as above to methylene groups by Wittig reaction, and hydroborating the resulting product followed by oxidation.

According to an eighth aspect of the present invention, there is provided a process for producing an optically active diphosphine oxide having a bicyclo[2.2.1]heptane skeleton of the formula (3) or (4) as above which comprises oxidizing an optically active diphosphine having a bicyclo[2.2.1]heptane skeleton of the formula (1) or (2) as above.

According to a ninth aspect of the present invention, there is provided a process for producing an optically active diphosphine of the formula (1) or (2) having a bicyclo[2.2.1]heptane skeleton as above which comprises reducing an optically active diphosphine oxide of the formula (3) or (4) as above.

According to a tenth aspect of the present invention, there is provided a process for producing an optically active diphosphine having a bicyclo[2.2.1]heptane skeleton of the formula (1) or (2) as above of high purity which comprises oxidizing an optically active diphosphine having a bicyclo[2.2.1]heptane skeleton of the formula (1) or (2) as above to an optically active diphosphine oxide having a bicyclo[2.2.1]heptane skeleton of the formula (3) or (4) as above, purifying the resulting oxide, and reducing the oxide thus purified, or a process for producing an optically active diphosphine having a bicyclo[2.2.1]heptane skeleton of the formula (1) or (2) as above of high purity which comprises converting the hydroxyl groups of an optically active diol having a bicyclo[2.2.1]heptane skeleton of the formula (9) or (10) as above to leaving groups, substituting the leaving groups with a phosphine compound to form an optically active diphosphine having a bicyclo[2.2.1]heptane skeleton of the formula (1) or (2) as above, converting the resulting diphosphine to an optically active diphosphine oxide having a bicyclo[2.2.1]heptane skeleton of the formula (3) or (4) as above, purifying the resulting oxide, and reducing the oxide thus purified.

DESCRIPTION OF THE PREFERRED EMBODIMENTS

The optically active diphosphine of the present invention of the formula (1) or (2),

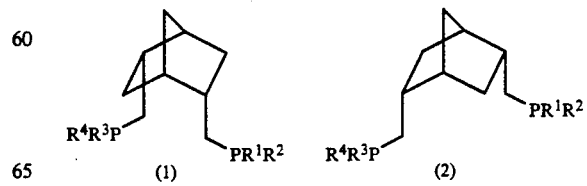
(1)  (2)

where $R^1$, $R^2$, $R^3$ and $R^4$ are as defined above, has fundamentally a bicyclo[2.2.1] skeleton and two methylene groups at the 2-and 5-positions thereof, at endo and endo configurations, respectively, and further, a phosphorus atom attached to each of these methylene groups.

Said optically active diphosphine is a ligand designed very precisely as mentioned above.

Many known diphosphine ligands having a capability of bidentate coordination such as 2,3-O-isopropylidene-2,3-dihydroxy-1,4-bis(diphenylphosphino)butane (abbreviated as "DIOP") and the like have been analyzed with respect to the steric structure.

It has been confirmed that when the diphosphine coordinates to a metal, a bite angle (phosphorus-metal-phosphorus) of about 90° or less is the stablest bite angle.

On the contrary, optically active diphosphine ligands having a bicyclo[2.2.1]heptane skeleton have not yet been analyzed in detail, but according to the calculation by C. P. Casey et al, the bite angle (phosphorus-metal-phosphorus) is about 120° (when the ligand coordinates to a metal), in which the strain energy exerting on the ligand is the lowest and the coordination is the most stabilized.

According to a calculation similar to that as above, it is concluded that the ligand of the above-mentioned DIOP can not have such a large bite angle.

Therefore, the diphosphine ligand of the present invention is made by a completely new design and is a chiral ligand having a fundamental skeleton of $C_2$ symmetry.

The present invention further provides a unique production route for producing the optically active diphosphine designed under the novel concept, a metal complex having the optically active diphosphine ligand and novel intermediates for preparing an optically active compound.

With respect to the definition of $R^1$, $R^2$, $R^3$ and $R^4$, the passage "$R^1$ and $R^2$ and/or $R^3$ and $R^4$ may be bonded directly or through at least one atom other than phosphorus to form a ring together with the phosphorus to which $R^1$ and $R^2$, or $R^3$ and $R^4$ attach" may be represented by the following formula (13) and (14)

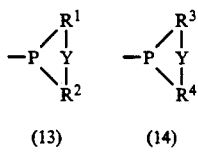

(13)  (14)

where Y is a direct bond, or an atom such as oxygen, nitrogen, metal and the like or an atom group such as carbon atom group, for example, alkylene (preferably $C_1$-$C_3$), arylene, alkylene containing an aromatic group and the like.

In the present invention, an optically active compound such as a diphosphine, an intermediate and the like generally means not only an optically pure, 100% ee optically active compound, but also a compound exhibiting substantially optical activity which can not be obtained by ordinary chemical syntheses and contains both enantiomers in different amounts.

According to the present invention, there is proposed a unique route for producing an optically active compound. For example, the route is as shown below.

Optically active endo-5-hydroxymethylbicyclo[2.2.1-]hept-2-ene of the formula (11) or (12),

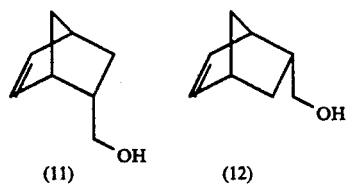

is epoxidized, subjected to intramolecular cyclizing etherification, and then the hydroxyl group is oxidized to give an optically active keto-ether of the formula (5) or (6),

The keto-ether is subjected to ring-opening to form an optically active keto-ol of the formula (7) or (8),

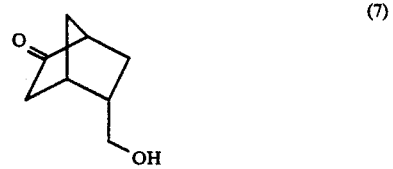

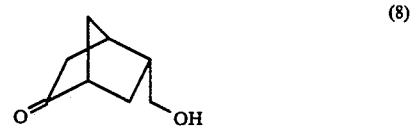

If desired, the hydroxyl group is appropriately protected, and the ketone group of the keto-ol is converted methylene group by Wittig reaction, and subjected to hydroboration and then oxidation to form an optically active diol having a bicyclo[2.2.1]heptane skeleton of the formula (9) or (10),

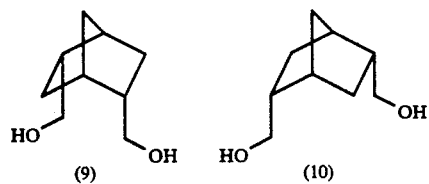

The hydroxyl group of the diol is converted to an appropriate leaving group, for example, p-toluenesulfonyloxy group as shown in the following formula (15),

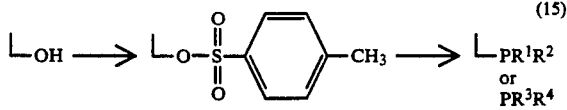

where $R^1$, $R^2$, $R^3$ and $R^4$ are as shown above. and then the leaving group is substituted with a phosphine compound to form an optically active diphosphine having a bicyclo[2.2.1]heptane skeleton of the formula (1) or (2)

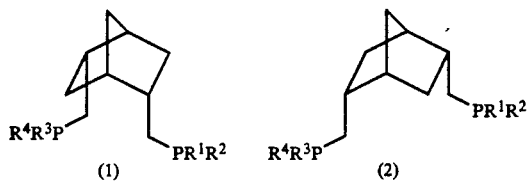

where $R^1$, $R^2$, $R^3$ and $R^4$ are as defined above.

It should be noted that it is not always necessary to start the route from the optically active endo-5-hydroxymethylbicyclo[2.2.1]hept-2-ene, formula (11) or (12), that is, the route may start from any intermediate in the route.

The resulting optically active diphosphine may be directly used for the preparation of a metal complex or as a ligand for catalytic reactions.

However, the present diphosphine is so unstable in air that it is easily oxidized unless it is handled and stored strictly in an anhydrous inert gas atmosphere. Therefore, the purification is fairly difficult and a lot of labor is required to obtain a highly pure diphosphine.

In view of the foregoing, the optically active diphosphine prepared as above is oxidized with an optional oxidizing agent to convert it to an optically active diphosphine oxide having a bicyclo[2.2.1]heptane skeleton of the formula (3) or (4),

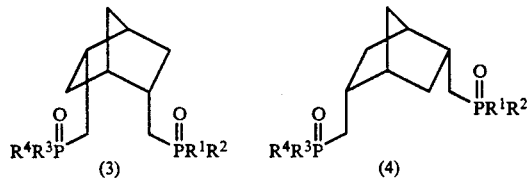

where $R^1$, $R^2$, $R^3$ and $R^4$ are as defined above.

The diphosphine oxide is stable at room temperature in air, and its isolation, purification and storage are easy.

In addition, it is also possible to prepare easily an optically active diphosphine of the formula (1) or (2) of high purity by isolating and purifying the corresponding diphosphine oxide and then reducing the oxide with an appropriate reducing agent.

A fundamental starting material in the present invention, optically active endo-5-hydroxymethylbicyclo[2.2.1]hept-2-ene may be prepared by various known methods.

For example, according to an optical resolution method described in Bull. Chem. Soc. Jpn., Vol. 46, pp. 888–892 (1973), endo-5-carboxybicyclo[2.2.1]hept-2-ene is converted to the cinconidine salt and recrystallization of the product from an acetone solvent is repeated to give a sparingly soluble (−)-form of the carboxylic acid salt. The resulting salt is separated and reduced to give (−)-endo-5-hydroxymethylbicyclo[2.2.1]hept-2-ene.

On the other hand, the (+)-form can be recovered from the easily soluble salt.

Further, according to a method recently actively researched, for example, a method described in Helv. Chim. Acta, Vol. 68, pp. 2100–2114 (1985), asymmetric Diels-Alder reaction of an acrylic acid ester derivative derived from (+)- or (−)- camphor with cyclopentadiene is carried out and the product is reduced with LiAlH$_4$ to prepare selectively (+)- or (−)-endo-5-hydroxymethylbicyclo[2.2.1]hept-2-ene.

According to the present invention, starting from the (+)- or (−)- enantiomer thus obtained, there may be produced an optically active diphosphine having the bicyclo[2.2.1]heptane skeleton as the end product.

Epoxidation of optically active endo-5-hydroxymethylbicyclo[2.2.1]hept-2-ene can be carried out by various known epoxidizing reactions, but it is preferable to use a reaction agent capable of epoxidation at a temperature as low as possible so as to prevent cleavage of the skeleton and isomerization. Such preferable reagents include organic performic acid, peracetic acid, perpropionic acid, perbenzoic acid, m-chloroperbenzoic acid, trifluoroperacetic acid, monoperphthalic acid and the like, and aqueous hydrogen peroxide and the like.

After epoxidation, the resulting product is isolated and purified, or if desired, without isolation and/or purification, and treated with acid or base to cause easily intramolecular cyclizing etherification resulting in forming 7-oxatricyclo[3.2.1.1$^{3,8}$]-2-nonanol.

The hydroxy group of the nonanol is oxidized to form an optically active keto-ether of the formula (5) or (6),

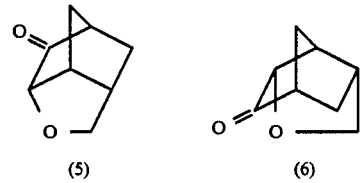

that is, optically active 7-oxatricyclo[3.2.1.1$^{3,8}$]-2-nonanone.

Oxidation of the hydroxyl group of 7-oxatricyclo[3.2.1.1$^{3,8}$]-2-nonanol is preferably carried out by a selective and mild oxidation reaction so as to avoid cleavage of the ring and isomerization, and therefore, there is preferably used Swern oxidation, Jones oxidation or the like which has been heretofore used for selective oxidation of the hydroxyl group of polycyclic compounds.

Then, the ether bond of the nonanol may be cleaved with aluminum amalgam to form a keto-ol of the formula (7) or (8),

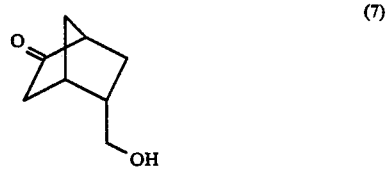

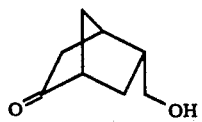

that is, optically active endo-5-hydroxymethylbicyclo[2.2.1]-2-heptanone.

The resulting hydroxyl group is protected by converting it to acetyloxy group, benzoyloxy group, trialkyloxy group or the like according to a conventional method.

The ketone group may be changed to an exo-methylene group by Wittig reaction, subjected to hydroborationoxidation treatment, and then the protecting group is removed to form optically active diol having a bicyclo[2.2.1]heptane skeleton of the formula (9) or (10),

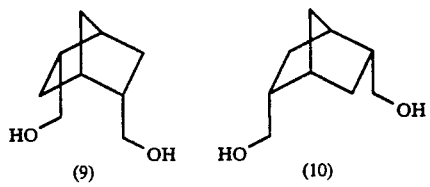

that is, optically active endo, endo-2,5-bis(hydroxymethyl)bicyclo[2.2.1]heptane.

The resulting diol may be converted to an optically active diphosphine having a bicyclo[2.2.1]heptane skeleton of the formula (1) or (2)

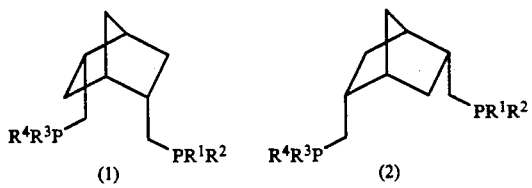

$R^1$, $R^2$, $R^3$ and $R^4$ are as defined above, by following a conventional method, for example, converting the hydroxyl group to a leaving group such as p-toluenesulfonyloxy group, trifluoromethylsulfonyloxy group and the like and then substituting the leaving group with a desired phosphine.

The resulting diphosphine may be purified through diphosphine oxide, if desired. For example, after removing separable reaction agents and by-products from the diphosphine, the diphosphine thus treated is substantially completely oxidized with an oxidizing agent, for example, an organic peroxide such as tert-butylhydroperoxide, cumene hydroperoxide and the like, aqueous hydrogen peroxide, and oxygen to form a diphosphine oxide.

The diphosphine oxide thus prepared is once isolated and purified by means of elution chromatography or the like, and then reduced to give a highly pure diphosphine. The conversion of the diphosphine oxide to the diphosphine may be effected by a conventional reducing method, for example, reduction with trichlorosilane in the presence of an amine such as triethylamine and the like, and reduction with hexachlorodisilane, and the like.

Exemplary suitable phosphine compounds contributing a moiety to the diphosphine compound of the present invention, said moiety enabling the diphosphine compound to function as a ligand, include:
alkyl phosphines such as
dimethylphosphine,
diethylphosphine,
dipropylphosphine,
dibutylphosphine,
dicyclohexylphosphine,
and the like;
aryl phosphines such as
diphenylphosphine,
dinaphthylphosphine,
di-m-tolylphosphine,
di-o-tolylphosphine,
bis(m-sulfonylphenyl)phosphine,
bis(6-methyl-2-naphthyl)phosphine,
bis(6-methoxy-2-naphthyl)phosphine,
and the like;
aralkyl phosphines such as
dibenzylphosphine,
bis(naphthylmethyl)phosphine,
bis(m-methylbenzyl)phosphine,
bis(o-methylbenzyl)phosphine,
bis(m-sulfonylbenzyl)phosphine,
bis(6-methyl-2-naphthylmethyl)phosphine,
bis(6-methoxy-2-naphthylmethyl)phosphine,
and the like; and
cyclic phosphines such as
diphenylenephosphine
and the like.

Further exemplary suitable phosphine compounds having different substituents include:
alkyl aryl phosphines such as
methylphenylphosphine,
t-butylphenylphosphine,
cyclohexylphenylphosphine,
cyclohexylnaphthylphosphine,
and the like;
alkyl aralkyl phosphines such as
methylbenzylphosphine,
cyclohexylbenzylphosphine,
methyl(naphthylmethyl)phosphine,
cyclohexyl(naphthylmethyl)phosphine,
and the like; and
aryl aralkyl phosphines such as
phenylbenzylphosphine,
phenyl(naphthylmethyl)phosphine,
naphthylbenzylphosphine,
naphthyl(naphthylmethyl)phosphine,
and the like.

The diphosphine compounds of the present invention are optically active compounds. When the diphosphine compounds are used as ligands to produce complexes of various metals, there can be produced optically active metal complexes.

When the optically active metal complex is used as a catalyst for a chemical reaction by which chirality is formed in the product from a prochiral starting material, the optically active metal complex exhibits both the catalytic activity of the racemic metal complex and a new catalytic asymmetric induction.

The center metal to which the diphosphine compound coordinates is usually an element of the platinum group such as ruthenium, rhodium, palladium, osmium, iridium, and platinum. In addition, the center metal can be a transition metal such as iron, cobalt, nickel and the like.

Optically active metal complexes having the diphosphine of the present invention as a ligand can be produced by conventional methods known as to each metal.

The metal complex catalysts having the diphosphine of the present invention as a ligand can be used for various catalytic asymmetric reactions such as asymmetric hydrogenation, asymmetric hydroformylation, asymmetric hydrosilylation, and the like, and further provide asymmetric synthetic reactions of high needs at present with a useful and fundamental catalyst technique.

According to the present invention, there is provided a novel optically active diphosphine having a bicyclo ring of which fundamental skeleton is of $C_2$ symmetry, and further a useful process for producing optically active compounds.

The following examples are given for the purpose of illustration and not by way of limitation.

EXAMPLE 1

Preparation of optically active (1S, 5S)-7-oxatricyclo[3.2.1.1$^{3,8}$]-2- nonanone Optically active (5S)-5-hydroxymethylbicyclo[2.2.1]hept-2-ene (17.6 mmol) ($[\alpha]_D$ −82.3°; ethanol, c=1.738) (2.1 g) was dissolved in 70 ml of methylene chloride, cooled to −10° C., and 4.57 g of an 80% m-chloroperbenzoic acid (21.2 mmol) was added to the solution thus cooled.

The resulting mixture was stirred at room temperature for 2.5 hours and washed with a saturated aqueous solution of sodium thiosulfate and a saturated aqueous solution of sodium bicarbonate, and the water phase was extracted with methylene chloride. The organic phases thus obtained were combined, washed with saturated brine and concentrated.

The concentrated residue was dissolved in 20 ml of tetrahydrofuran and 10 ml of a 10% aqueous solution of hydrochloric acid was added to the resulting mixture and stirred for 15 min. followed by adding diethylether and brine, and the organic layer was separated and the water layer was extracted with diethylether. The resulting organic layers were combined, washed with saturated brine, dried over anhydrous magnesium sulfate, concentrated, and the resulting residue was directly used to the next reaction.

(COCl)$_2$ (37.8 mmol) (3.30 ml) was dissolved in 60 ml of dried methylene chloride, and to the resulting solution was added a solution of dried dimethylsulfoxide (75.6 mmol) (5.36 ml) in methylene chloride at −60° C. followed by stirring for further 15 min.

Triethylamine (227 mmol) (31.6 ml) was added to the resulting solution over 5 min. and then returned to room temperature, and stirred for a further hour followed by adding 30 ml of water to separate an organic layer.

The water layer was subjected to extraction with methylene chloride. The organic layers were combined, washed with 3N hydrochloric acid, saturated aqueous sodium bicarbonate, and saturated brine, and dried over anhydrous magnesium sulfate.

The resulting product was concentrated and purified by flash chromatography (silica gel, ethyl acetate/hexane=$\frac{1}{2}$) to obtain 1.86 g of a solid matter (yield, 76%) mp. 93°-95° C.;

$[\alpha]_D$+156.4° (CHCl$_3$, c=1.01);

$^1$H NMR (90 MHz, CDCl$_3$) 1.30-3.03 (m, 6 H), 2.07 (ddd, J=4.4 Hz, 12.7 Hz, 10.6 Hz, 1 H, b), 3.78 (d, J=8.8 Hz), 3.87 (d, J=6.37 Hz), 4.00 (dd, J=4.4 Hz, 8.4 Hz); IR 2952, 2876, 1755, 1130, 1055, 1014, 938, 901, 865, 465 cm$^{-1}$.

EXAMPLE 2

Preparation of optically active (5S)-5-hydroxymethylbicyclo[2.2.1]-2-heptanone 1 93 g of Al powder (72.4 mmol) and 0.79 g of HgCl$_2$ (2.9 mmol) were placed in 100 ml of dried benzene, stirred at room temperature for one hour, cooled with ice, and to the resulting mixture was added a solution of 1.83 g of optically active (1S, 5S)-7-oxatricyclo[3.2.1.1$^{3,8}$]-2-nonanone (13.4 mmol) in 30 ml of dried methanol.

The resulting mixture was stirred at 0° C. for 2 hours, then in a water bath at room temperature for further 2 hours, filtered with celite and washed with ethyl acetate. The filtrate was concentrated and purified by flash chromatography (silica, ethyl acetate/hexane=1/1).

Yield 0.76 g (41%); recovered starting material 0.89 g (48%).

$[\alpha]_D$−2.6° (ethanol, c=1.15);

$^1$H NMR (90 MHz, CDCl$_3$) 0.96-2.74 (m, 10 H), 3.51 (dd, J=8.1 Hz, 10.5 Hz), 3.71 (dd, J=6.6 Hz, 10.5 Hz); IR 3404, 2954, 2872, 1739, 1409, 1058, 1039, 1013 cm$^{-1}$.

EXAMPLE 3

Preparation of optically active (2S, 5S)-2,5-bishydroxymethylbicyclo[2.2.1]heptane 0.80 g of optically active (5S)-5-hydroxymethylbicyclo[2.2.1]-2-heptanone (5.7 mmol) and 0.011 g of p-toluenesulfonic acid (0.057 mmol) were dissolved in 35 ml of methylene chloride. To the resulting solution was added 0.63 ml of 3,4-dihydro-2H-pyran (6.9 mmol), stirred at room temperature, neutralized with aqueous NaOH while cooling with ice, and then extracted with ether.

The organic layer was washed with saturated brine, dried over anhydrous magnesium sulfate and concentrated. The resultant product was directly used for the next reaction.

0.81 g of 55% sodium hydride (18.6 mmol) was added to 20 ml of dried dimethylsulfoxide and stirred at 75°-80° C. When the resulting solution became transparent, a solution of 6.24 g of methyltriphenylphosphonium iodide (15.4 mmol) in 30 ml of dimethylsulfoxide was added thereto at 0° C. and stirred at room temperature for one hour.

To the resulting solution was added a solution of the above-mentioned unpurified optically active (5S)-5-hydroxymethylbicyclo[2.2.1]-2-heptanone with protected hydroxyl group in 10 ml of dried dimethylsulfoxide and stirred for 1 hour.

50 ml of diethylether was added thereto and the resulting organic layer was washed with 30 ml of water 4 times.

The water layer was subjected to extraction with diethylether and the resulting diethylether layer was washed with water, and the organic layers were combined, washed with saturated brine and dried over anhydrous magnesium sulfate. The product thus dried was concentrated, passed through a short-pass column (silica gel, diethylether/hexane=1/30), and concentrated again and then directly used for the next reaction.

The concentrated solution was dissolved in 30 ml of dried tetrahydrofuran. To the resulting solution was added 5.04 ml of a 0.5 mol/l borane tetrahydrofuran complex (2.52 mmol) while cooling with ice and stirred for 0.5 hour.

A 3N aqueous sodium hydroxide (2 ml) cooled with ice was added and then 8 ml of 30% aqueous hydrogen peroxide was added, and stirring was effected for 12 hours.

The resulting mixture was treated with a saturated aqueous sodium thiosulfate while cooling with ice, stirred for one hour, once concentrated and the water layer was extracted with methylene chloride 5 times. The extract was washed with saturated brine and dried over anhydrous magnesium sulfate.

The resulting solution was concentrated. 50 ml of methanol and 0.012 g of p-toluenesulfonic acid (0.063 mmol) were added thereto and stirred. Then ice and a saturated aqueous sodium bicarbonate were added to neutralize, and the solution thus neutralized was concentrated once, and extracted with methylene chloride 5 times. The extract was washed with saturated brine, dried over anhydrous magnesium sulfate, concentrated, and purified by flash chromatography (silica gel, ethyl acetate/hexane=2/1) to give crystals. Further, the crystals were recrystallized with a solvent of benzene/chloroform=2/1.

mp. 116.9°–117.3° C.;

$[\alpha]_D + 28.3°$ (ethanol, c=0.842);

$^1$H NMR (500 MHz, CDCl$_3$) 1.02 (dd, J=5.2 Hz, 12.3 Hz, 2 H), 1.50 (s. 2 H), 1.47–1.60 (m, 4 H), 2.10 (bs, 2 H) 2.27 (s, 2 H), 3.58 (dd, J=10.5, 8.7 Hz, 2 H), 3.66 (dd, J=10.5 Hz, 6.9 Hz, 2 H);

$^{13}$C NMR (22.5 MHz, CDCl$_3$) 25.0, 38.1, 41.2, 42.8, 63.7; IR (KBr) 3248, 2954, 2860, 1432, 1348, 1215, 1059, 1009, 942, 913, 675, 586 cm$^{-1}$.

EXAMPLE 4

Preparation of optically active (2S, 5S)-2,5-bis(toluenesulfonyloxymethyl)bicyclo[2.2.1-]heptane In a mixture solvent of 3.6 ml of pyridine and 8 ml of chloroform was dissolved 1.25 g of optically active (2S, 5S)-2,5-bishydroxymethylbicyclo[2.2.1]heptane (7.97 mmol), and 4.56 g of p-toluenesulfonyl chloride (23.9 mmol) was added thereto followed by stirring for one hour at room temperature.

Ice water and 10 ml of 3N hydrochloric acid were added thereto and the resulting aqueous solution was extracted with ether. The organic layers were combined, washed with a saturated aqueous sodium bicarbonate and saturated brine, and dried with anhydrous magnesium sulfate.

After concentration, the residue was purified by flash chromatography (silica gel, ethyl acetate/hexane=1/4) to give white crystals, and the crystals were recrystallized from a mixture solvent of chloroform/hexane=1/4.

mp. 108.8°–109.2° C.;

$[\alpha]_D + 4.2°$ (CHCl$_3$, c=0.908);

$^1$H NMR (90 MHz, CDCl$_3$) 0.65–2.23 (m, 10 H), 2.46 (s, 6 H), 3.87 (d, J=8.57 Hz, 2 H), 3.91 (d, J=6.59 Hz, 2 H), 7.35 (d, J=8.1 Hz, 4 H), 7.78 (d, J=8.1 Hz, 4 H);

$^{13}$C NMR (50 MHz, CDCl$_3$) 21.7, 24.5, 38.4, 39.2, 40.9, 70.9, 128.2, 130.3, 133.3, 145.3;

IR (KBr); 1354, 1187, 1171, 946, 867, 835, 812, 665, 555 cm$^{-1}$.

EXAMPLE 5

Preparation of optically active (2S, 5S)-2,5-bis((di-phenylphosphino)methylbicyclo[2.2.1-]heptane An alloy of 356 mg of potassium (9.36 mmol) and 84 mg of sodium (2.34 mmol) was placed in a Schlenk tube in dried argon atmosphere. 13 ml of dried dioxane and 800 mg of triphenylphosphine (3.05 mmol) were added thereto and stirred vigorously at room temperature for 4 hours.

To the resulting mixture was added a solution of 600 mg of optically active (2S, 5S)-2,5-bis(toluenesulfonyloxymethyl)bicyclo[2.2.1]heptane (1.29 mmol) in 6 ml of dried toluene, and stirred at room temperature for 12 hours.

The resulting reaction solution was treated with ice-ethanol, diluted with 30 ml of methylene chloride and 5 ml of an aqueous 3N hydrochloric acid, and the water layer was extracted with methylene chloride.

The organic layers were combined, washed with saturated aqueous sodium bicarbonate and saturated brine, dried over anhydrous magnesium sulfate, and concentrated to give a raw title compound. The resulting title compound was once oxidized to form the corresponding optically active diphosphine oxide and then reduced to purify to give the highly pure compound.

The above-mentioned raw diphosphine was dissolved in 8 ml of chloroform. 2.2 ml of 30% hydrogen peroxide was added thereto and stirred at room temperature for 10 hours. Then a saturated aqueous sodium thiosulfate was added at 0° C. to treat the resulting mixture and diluted with 30 ml of chloroform.

The water layer was extracted with chloroform. The resulting organic layers were combined, washed with a saturated aqueous sodium bicarbonate and saturated brine and dried over anhydrous magnesium sulfate.

The resulting solution was concentrated and the residue was purified with flash chromatography (silica gel, 2% methanol/chloroform) to obtain 340 mg of colorless crystals (Yield, 58%).

Data obtained by instrumental analysis of the optically active diphosphine oxide were as shown below.

mp. 200.2°–201.0° C.;

$[\alpha]_D + 28.2°$ (CHCl$_3$, c=0.966);

$^1$H NMR (500 MHz, CDCl$_3$) 1.03 (dd, J=4.5, 13.4 Hz, 2 H), 1.28 (s, 2 H), 1.56 (dt, 4.5, 11.9 Hz, 2 H), 1.92 (s, 2 H), 2.23–2.37 (m, 6 H);

$^{13}$C NMR (125 MHz, CDCl$_3$) 29.6 (d), 31.0 (d), 37.5 (d), 41.5 (s), 42.2 (d);

$^{31}$P NMR (200 MHZ, CDCl$_3$, external H$_3$PO$_4$) 32.2 (s).

In dried acetonitrile was dissolved 300 mg of the above-mentioned diphosphine oxide (0.69 mmol). 0.96 ml of triethylamine and 938 mg of trichlorosilane (6.93 mmol) were added and heated at 80°–90° C. with stirring for one day. Then the resulting product was treated with 15 ml of a 25% aqueous sodium hydroxide, and acetonitrile was removed in vacuo. The product was extracted with toluene and dried over anhydrous magnesium sulfate. After concentration, the concentrate was purified by column chromatography (silica gel, ether/hexane=1/50) and 275 mg of the title optically active diphosphine was obtained.

mp. 84.0°–85.0° C.;

$[\alpha]_D + 27.6°$ (CHCl$_3$, c=0.696);

1H NMR (500 MHz, CDCl3) 1.18 (dd, J=5.0, 13.5 Hz, 2 H), 1.30 (s, 2 H), 1.60 (dt, 5.0, 10.5 Hz, 2 H), 1.85 (bs, 2 H), 2.08-2.17 (m, 6 H) 7.13-7.45 (m, 20 H);

13C NMR (125 MHz, CDCl3) 29.62 (d, J=7.6 Hz), 30.99 (d, J=12.4 Hz), 37.52 (d, J=13.4 Hz), 41.54 (s), 42.18 (d, J=9.4 Hz) and aromatic signals;

31P NMR (200 Mhz, CDCl3, external H3PO4) −17.68.

EXAMPLE 6

Application to the preparation of an optically active metal complex

To a mixture solution of 0.06 ml of 70% HClO4 and 0.8 ml of distilled tetrahydrofuran was added a solution of 202 mg of norbornadiene(acetylacetonato)rhodium(I) (0.69 mmol) in 12.4 ml of dried tetrahydrofuran, and the resulting mixture solution was stirred for 40 min. at room temperature.

To the resulting solution was added a solution of 338 mg of optically active (2S, 5S)-2,5-bis((diphenylphosphino)methyl)bicyclo[2.2.1]heptane (0.69 mmol) in 2 ml of dried tetrahydrofuran, and stirred at room temperature for further 1.5 hour.

Then, 14 ml of diethylether was added and stirring was effected at room temperature for further 20 hours to give crystals, which were filtered off to obtain 450 mg of yellow crystals of (norbornadiene)[(2S, 5S)-2,5-bis ((diphenylphosphino)methyl)bicyclo[2.2.1]heptane]rhodium(I) perchlorate (Yield, 83%).

31P NMR (200 Mhz, CDCl3, external H3PO4) 23.0 (d, J=152.7 Hz).

EXAMPLE 7

Preparation of optically active metal complex 182 mg of norbornadiene(acetylacetonato)rhodium(I) (0.62 mmol) was dissolved in 3 ml of dried tetrahydrofuran and 0.13 ml of 42% HBF4 was added, and the resulting solution was stirred at room temperature for 45 min.

278 mg of optically active (2S, 5S)-2,5-bis((diphenylphosphino)methyl)bicyclo[2.2.1]heptane (0.56 mmol) was added thereto and stirred at room temperature for further 1.5 hour. Then, 15 ml of diethylether was added and stirred at room temperature for further one hour resulting in the formation of crystals, followed by filtration to give 395 mg of crystals of (norbornadiene)[(2S, 5S)-2,5-bis((diphenylphosphino)methyl)bicyclo[2.2.1-]heptane]rhodium(I) tetrafluoroborate (Yield, 85%). $[\alpha]_D$+9.02° (CH2Cl2, c=1.0)

REFERENCE EXAMPLE 1

Preparation of optically active (5S)-5-hydroxymethylbicyclo[2.2.1]hept-2-ene

The title compound which is a starting material in Example 1 may be prepared by the following method.

In 25 ml of methylene chloride was dissolved 628 mg (2.12 mmol) of (1R, 2S, 3R)-3-(2,2-dimethylpropoxy)-4,7, 7-trimethylbicyclo[2.2.1]hept-2-yl acrylate prepared by the method of W. Oppolzer et al described in Helv. Chim. Acta, Vol. 68, pp. 2100-2114 (1985).

To the resulting solution was added 3.2 ml (3.2 mmol) of a 1.0 mol/l solution of dichlorodiisopropoxytitanium (TiCl2 (i-PrO)2) in methylene chloride at −20° C., stirred for one hour, and 6.4 ml (6.4 mmol) of a 1.0 mol/l solution of cyclopentadiene purified by distillation immediately before using in methylene chloride was added thereto and stirred at −20° C. for 4 hours.

After concentration of the reaction fluid, the Diels-Alder reaction product was obtained by column chromatography.

The resulting Diels-Alder addition product was reduced with 100 mg (2.63 mmol) of LiAlH4 in 20 ml of diethylether solvent and the reaction fluid was hydrolyzed, extracted with diethylether.

The extract was dried and concentrated to obtain a raw product. The raw product was purified by column chromatography to give the title compound. 232 mg (1.87 mmol), yield 88%, $[\alpha]_D$= −82.3°.

What is claimed is:

1. An optically active keto-ether of the formula (5) or (6)

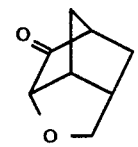
(5)

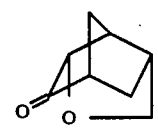
(6)

2. An optically active keto-ol of the formula (7) or (8)

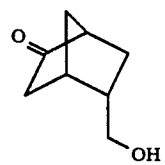
(7)

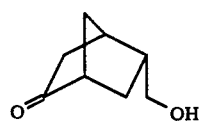
(8)

3. A process for producing an optically active keto-ol of claim 2 which comprises ring opening of an optically active keto-ether of the formula (5) or (6)

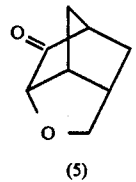
(5)

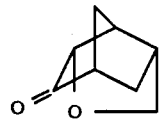
(6)

4. A process for producing an optically active keto-ether of claim 1 which comprises epoxidizing an optically active endo-5-hydroxymethylbicyclo[2.2.1]hept-2-ene of the formula (11) or (12)

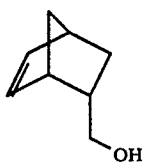
(11)

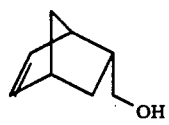
(12)

subjecting the resulting epoxide to an inner molecular cyclizing etherification and oxidizing the hydroxyl group.

* * * * *